US007446190B2

(12) United States Patent
Sadelain et al.

(10) Patent No.: US 7,446,190 B2
(45) Date of Patent: Nov. 4, 2008

(54) NUCLEIC ACIDS ENCODING CHIMERIC T CELL RECEPTORS

(75) Inventors: Michel Sadelain, New York, NY (US); Renier Brentjens, Maplewood, NJ (US); John Maher, Surrey (GB)

(73) Assignee: Sloan-Kettering Institute for Cancer Research, New York, NY (US)

( * ) Notice: Subject to any disclaimer, the term of this patent is extended or adjusted under 35 U.S.C. 154(b) by 458 days.

(21) Appl. No.: 10/448,256

(22) Filed: May 28, 2003

(65) Prior Publication Data

US 2004/0043401 A1    Mar. 4, 2004

Related U.S. Application Data

(60) Provisional application No. 60/383,872, filed on May 28, 2002.

(51) Int. Cl.
C07H 21/04    (2006.01)
(52) U.S. Cl. .................... 536/23.4; 536/23.53
(58) Field of Classification Search .............. None
See application file for complete search history.

(56) References Cited

U.S. PATENT DOCUMENTS

| | | | |
|---|---|---|---|
| 4,675,287 A | 6/1987 | Reisfeld et al. | |
| 4,769,331 A | 9/1988 | Roizman et al. | |
| 4,859,587 A | 8/1989 | Roizman | |
| 4,946,778 A | 8/1990 | Ladner et al. | |
| 5,302,370 A | 4/1994 | Neumeier et al. | |
| 5,328,688 A | 7/1994 | Roizman | |
| 5,359,046 A | 10/1994 | Capon et al. | |
| 5,405,990 A | 4/1995 | Burke et al. | |
| 5,585,096 A | 12/1996 | Martuza et al. | |
| 5,686,281 A | 11/1997 | Roberts | |
| 5,728,379 A | 3/1998 | Martuza et al. | |
| 6,051,428 A | 4/2000 | Fong et al. | |
| 6,344,445 B1 | 2/2002 | Boursnell et al. | |
| 2003/0077249 A1* | 4/2003 | Bebbington et al. ........ | 424/93.2 |

FOREIGN PATENT DOCUMENTS

| | | |
|---|---|---|
| WO | WO96/29421 A1 | 9/1996 |
| WO | WO97/00085 A1 | 1/1997 |
| WO | WO97/34634 A1 | 9/1997 |

OTHER PUBLICATIONS

Kroczek et al., 2005, J. Allergy Clin. Immunol, 116: 906-909.*
Clarkson et al., 2005, Transplantation, 80: 555-563.*
Oki et al., 2005, Molecular Cell, 19: 707-716.*
Maher et al., 2002, Nature Biotechnology, 20: 70-75.*
Alvarez-Vallina et al., Antigen-specific targeting of CD28-mediated T cell co-stimulation using chimeric single-chain antibody variable fragment-CD28 receptors, Eur. J. Immunol., 1996, pp. 2304-2309, vol. 26.
Amit et al., Three-Dimensional Structure of an Antigen-Antibody Complex at 2.8 Å Resolution, Science, 1986, pp. 747-753, vol. 233.

Dranoff et al., Vaccination with irradiated tumor cells engineered to secrete murine granulocyte-macrophage colony-stimulating factor stimulates potent, specific, and long-lasting anti-tumor immunity, Proc. Natl. Acad. Sci. USA, 1993, pp. 3539-3543.
Feldhaus et al., A CD2/CD28 chimeric receptor triggers the CD28 signaling pathway in CTLL.2 cells, Gene Therapy, 1997, pp. 833-838, vol. 4.
Karpoff et al., Prevention of Hepatic Tumor Metastases in Rats with Herpes Viral Vaccines and γ-Interferon, J. Clin. Invest., 1997, pp. 799-804, vol. 99, No. 4.
Kutubuddin et al., Eradication of preexisting murine tumor using herpes amplicon vectors, Cancer Gene Therapy, 1997, pp. S26 XP002073450, vol. 4, No. 6.
Lewin, Genes IV, 1990, pp. 810, Publisher: Oxford University Press.
Panka et al., Variable region framework differences result in decreased or increased affinity of variant anti-digoxin antibodies, Proc. Natl. Acad. Sci. USA, 1988, pp. 3080-3084, vol. 85.
Parijs, Homeostasis and Self-Tolerance in the Immune System: Turning Lymphocytes off, Science, 1998, pp. 243-248, vol. 280.
Paul, Fundamental Immunology, 1993, pp. 553-554, Publisher: Raven Press.
Rudikoff et al., Single amino acid substitution altering antigen-binding specificity, Proc. Natl. Acad. Sci. USA, 1982, pp. 1979-1983, vol. 79.
Sambrook, Molecular Cloning, a Laboratory Manual, 1989, pp. 16.9 & 16.11, Publisher: Cold Spring Harbor Laboratory.
Tung et al., Rapid Production of Interleukin-2-Secreting Tumor Cells by Herpes Simplex Virus-Mediated Gene Transfer: Implications for Autologous Vaccine Production, Human Gene Therapy, 1996, pp. 2217-2224, vol. 7.
Hellstrom et al., Tumor vaccines—a reality at last?, Journal of Immunotherapy, 1998, pp. 119-126, vol. 21, No. 2.
Stevenson FK., Tumor vaccines, FASEB J., 1991, pp. 2250-2257, vol. 5, No. 9.
Vieweg et al., Considerations for the use of cytokine-secreting tumor cell preparations for cancer treatment, Cancer Investigation, 1995, pp. 193-201, vol. 13, No. 2.

* cited by examiner

*Primary Examiner*—Ilia Ouspenski
(74) *Attorney, Agent, or Firm*—Marina Larson & Associates, LLC

(57) ABSTRACT

Chimeric T cell receptors (TCR) are provided that combine, in a single chimeric species, the intracellular domain of CD3 ζ-chain, a signaling region from a costimulatory protein such as CD28, and a binding element that specifically interacts with a selected target. When expressed, for example in T-lymphocytes from the individual to be treated for a condition associated with the selected target, a T cell immune response is stimulated in the individual to the target cells. The chimeric TCR's are able to provide both the activation and the co-stimulation signals from a single molecule to more effectively direct T-lymphocyte cytotoxicity against the selected target and T-lymphocyte proliferation.

13 Claims, 8 Drawing Sheets

US 7,446,190 B2

NUCLEIC ACIDS ENCODING CHIMERIC T CELL RECEPTORS

CROSS REFERENCE TO RELATED APPLICATIONS

This application claims the benefit of U.S. Provisional Application No. 60/383,872, filed May 28, 2002, which is incorporated herein by reference.

BACKGROUND OF INVENTION

This application relates to nucleic acid polymers encoding chimeric T cell receptors (TCRs), to the chimeric TCRs, and to methods of using same to facilitate a T cell response to a selected target.

The induction of potent tumor immunity presents a major challenge for cancer immunotherapy. Tumor cells have many properties that facilitate immune evasion 1-3. Most tumor antigens characterized to date are self-antigens and are thus poorly immunogenic 4,5. The paucity of target antigens, the difficulty of overcoming tolerance to self-antigens, and impaired antigen presentation also contribute to compromise T-cell priming in cancer-bearing hosts 1-3,6-10. Furthermore, malignant cells may escape from tumor-specific effector T cells by downregulating major histocompatibility complex (MHC) and/or antigen expression, or by establishing an immunosuppressive microenvironment 1-3,11.

Genetic approaches offer a potential means to enhance immune recognition and elimination of cancer cells. One promising strategy is to genetically engineer T lymphocytes to express artificial TCRs that direct cytotoxicity toward tumor cells 12,13. Artificial receptors typically comprise a tumor antigen-specific recognition element derived from a single-chain antibody variable fragment (scFv). When used to reprogram T-cell specificity, such fusion receptors permit MHC-independent recognition of native rather than processed antigen 12-14. ScFv-based TCRs are engineered to contain a signaling domain that delivers an activation stimulus (signal 1) only 12-14. The TCR-ζ cytoplasmic domain, which delivers a potent signal 1 in the absence of the remaining components of the TCR-CD3 complex 15,16, is well suited for activating cytolytic functions. The potential clinical utility of this strategy is supported by the demonstration that, despite fears about defective signaling in lymphocytes of tumor-bearing subjects 17, ζ-chain fusion receptors retain potent activity in cancer patent cytotoxic T cells 18.

However, while sufficient to elicit tumoricidal functions, the engagement of ζ-chain fusion receptors may not suffice to elicit substantial IL-2 secretion in the absence of a concomitant co-stimulatory signal 18. In physiological T-cell responses, optimal lymphocyte activation requires the engagement of one or more co-stimulatory receptors (signal 2), the best characterized of which is CD28 19-22. Provision of signal 1 in the absence of CD28 signaling can result in a very poor T-cell proliferative response or in the induction of anergy or apoptosis 19-22. Consequently, it may be extremely valuable to engineer human T cells so that they receive a co-stimulatory signal in a tumor antigen-dependent manner. An important development in this regard has been the successful design of scFv-CD28 fusion receptors that transduce a functional antigen-dependent co-stimulatory signal in human primary T cells, permitting sustained T-cell proliferation when both the endogenous TCR and the chimeric CD28 receptor are engaged 23. See U.S. patent application Ser. No. 08/940,544.

Notwithstanding the foregoing efforts, there remains a continuing need for more effective chimeric TCRs. The present invention offers chimeric TCRs that are able to provide both the activation and the co-stimulation signals from a single molecule to more effectively direct T-lymphocyte cytotoxicity against a defined target and T-lymphocyte proliferation. ζ

SUMMARY OF INVENTION

The present invention provides chimeric TCR's, nucleic acid polymer encoding the chimeric TCR's and methods of using the chimeric TCR's to facilitate T cell response to a specific target. The chimeric TCR's of the invention combine, in a single chimeric species, the intracellular domain of CD3 ζ-chain ("zeta chain portion"), a signaling region from a costimulatory protein such as CD28 and a binding element that specifically interacts with a selected target. Thus, in accordance with a first aspect of the invention, there is provided a nucleic acid encoding a chimeric T cell receptor, said chimeric T cell receptor comprising a zeta chain, a CD28 signaling region and a binding element that specifically interacts with a selected target. In accordance with a second aspect of the invention, there is provided a chimeric T cell receptor comprising a zeta chain portion, a CD28 signaling region and a binding element.

In accordance with the method of the invention a chimeric TCR is provided which comprises a zeta chain portion, a co-stimulatory signaling element and a binding element which specifically interacts with a cellular marker associated with target cells. T-lymphocytes from the individual to be treated, for example a human individual, are transduced with the chimeric TCR. This transduction may occur ex vivo, after which the transduced cells are reintroduced into the individual. As a result, T cell immune response is stimulated in the individual to the target cells.

BRIEF DESCRIPTION OF DRAWINGS

FIG. 3). (B) The P28z fusion receptor renders T lymphocytes capable of PSMA-dependent, B7.1-independent expansion following co-cultivation with LNCaP tumor calls. 19z1-, Pz1-, and Pz28-transduced T cells did not expand.

DETAILED DESCRIPTION

In accordance with the present invention, activation and co-stimulation are provided by a single chimeric T cell receptor comprising a zeta chain portion, a costimulatory signaling region and a target-specific binding element. The T cell receptor is suitably generated in situ in T lymphocytes by expression of a nucleic acid polymer encoding the three portions of the chimeric T cell receptor.

As used in the specification and claims of this application, the term "costimulatory signaling region" refers to it portion of the chimeric T cell receptor comprising the intracellular domain of a costimulatory molecule. Costimulatory molecules are cell surface molecules other than antigen receptors or their ligands that are required for an efficient response of lymphocytes to antigen. Examples of such molecules include CD28, 4-1BB, DAP-10 and ICOS. Thus, while the invention in exemplified primarily with CD28 as the co-stimulatory signaling element, other costimulatory elements are within the scope of the invention. For example, chimeric TCR containing the intracellular domain of 4-1BB (full sequence given in Seq ID No: 15), ICOS (full sequence given in Seq ID No: 16) and DAP-10 (full sequence given by Seq. ID No: 17) are also suitably employed in the invention.

Figure 1:
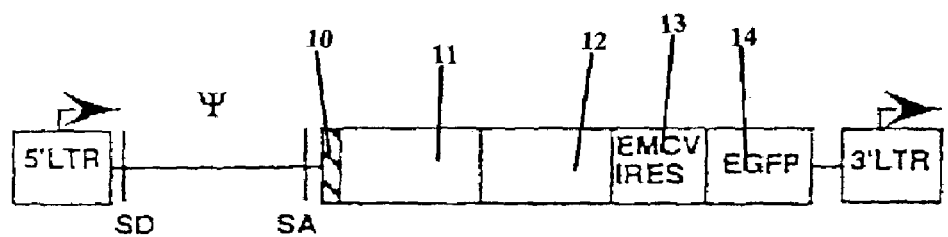
FIG. 1 shows a schematic of a nucleic acid polymer within the scope of the invention.

FIG. 1 shows a schematic of a nucleic acid polymer within the scope of the invention in which the T cell receptor is positioned within an SFG onco-retroviral vector. As shown, the nucleic acid polymer comprises the 5'-long terminal repeat (LTR) and the packaging signal ψ portion of the vector, followed by the CD8 α-hinge 10 and the binding element 11. SD and SA represent the splice donor and splice acceptor, respectively. The next region 12 encodes the zeta chain portion and CD28 sequences, and may additionally include transmembrane sequences from other sources, for example from CD8. The zeta and CD28 may be disposed in the nucleic acid polymer is either order. Next in order comes an EMCV IRES 13, followed by a sequence 14 encoding a marker protein, such as enhanced green fluorescent protein (EGFP). At the 3' end of the nucleic acid polymer as illustrated in FIG. 1 is a 3'-LTR from the SFG onco-retroviral vector. While the structure in FIG. 1 reflects the vector which was used in the examples described below, other vectors which result in expression of the chimeric TCR of the invention may also be employed.

The zeta chain portion sequence employed in the present application includes the intracellular domain. This domain, which spans amino acid residues 52-163 (Seq. ID No: 14 (nucleotides 154-489, Seq. ID No. 3) of the human CD3 zeta chain, can be amplified using the primers of Seq. ID Nos. 1 and 2.

CD28 sequences can be found in the present application on either side of the zeta chain portion sequence. In either case, the CD28 sequences include the signaling elements from CD28. In one embodiment, where CD 28 is between the zeta chain portion and the scFv, the CD28 portion suitably includes the transmembrane and signaling domains of CD28, i.e., the portion of CD28 cDNA spanning nucleotides 340 to 663, including the stop codon (amino acids 114-220 of Seq. ID No. 10). This portion of CD28 can be amplified by PCR using the primers of Seq. ID NO. 4 and 5. The full sequence of this region is set forth in Seq. ID No: 6. Alternatively, when the zeta sequence lies between the CD28 sequence and the binding element, the 41 amino acid intracellular domain of CD28 (amino acid residues given by Seq. ID No. 9) is suitably used alone. This fragment of CD28 cDNA can be amplified using primers of Seq. ID. Nos. 7 and 8.

Binding elements used in the invention are selected to provide the chimeric TCR with the ability to recognize a target of interest. The target to which the chimeric T cell receptors of the invention are directed can be any target of clinical interest to which it would be desirable to induce a T cell response. This would include markers associated with cancers of various types, including without limitation prostate cancer (for example using a binding element that binds to PSMA), breast cancer (for example using a binding element that targets Her-2) and neuroblastomas, melanomas, small cell lung carcinoma, sarcomas and brain tumors (for example using a binding element that targets GD 2). Known binding elements used in chimeric TCR's are generally useful in the present invention, and include without limitation those described in commonly assigned PCT Publication 97/36434 and U.S. patent application Ser. Nos. 08/940,544 and 09/786, 502 which are incorporated herein by reference in their entirety.

The binding elements used in the invention are suitably antibodies that recognize a selected target. For convenience, the antibody used as the binding element is preferably a single chain antibody (scFv). Single chain antibodies may be cloned from the V region genes of a hybridoma specific for a desired target. The production of such hybridomas has become routine, and the procedure will not be repeated here. A technique which can be used for cloning the variable region heavy chain (V-H-) and variable region light chain (V-L-) has been described in Orlandi et al., Proc. Natl. Acad. Sci. (USA) 86: 3833-3837 (1989). Briefly, mRNA is isolated from the hybridoma cell line, and reverse transcribed into complementary DNA (cDNA), for example using a reverse transcriptase polymerase chain reaction (RT-PCR) kit. Sequence-specific primers corresponding to the sequence of the V-H- and V-L-genes are used. Sequence analysis of the cloned products and comparison to the known sequence for the V-H- and V-L-genes can be used to show that the cloned V-H-gene matched expectations. The V-H- and V-L-genes are then attached together, for example using an oligonucleotide encoding a (gly-ser-2-)-5-linker.

As is reflected in the examples below, the transmembrane domain does not need to be the CD28 transmembrane domain, and indeed is CD28 in the embodiment with the centrally-positioned largely as a matter of convenience to minimize the number of amplification/cloning steps that need to be performed. Other transmembrane domains that may be employed include the CD8 and CD3 zeta transmembrane domains.

In addition to the zeta chain portion, CD28 and binding elements, the chimeric TCR may include a selection element. For example, dihydrofolate reductase (DHFR) may be included in the TCR to allow ex vivo or in vivo selection for transduced cells using methotrexate. (See commonly-assigned PCT Publication 97/33988, which is incorporated herein by reference).

Figure 2:
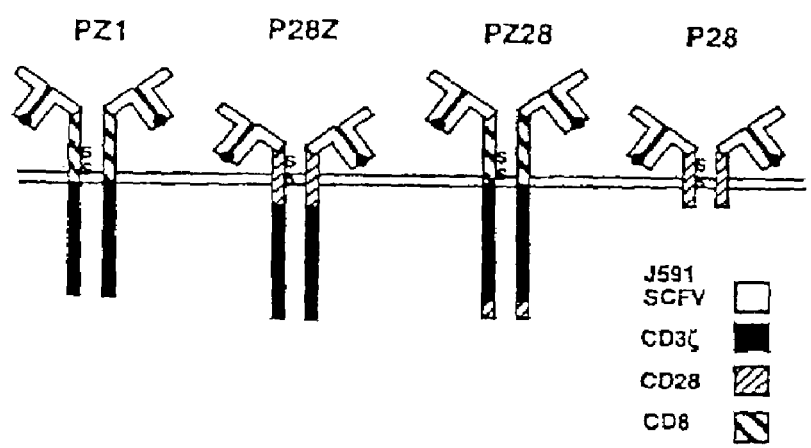
FIG. 2 shows a series of chimeric TCR's.

FIG. 2 shows a series of chimeric TCR's specific for PSMA that were prepared in order to evaluate the efficacy of the invention. TCR PZ1, a control species, contains a PSMA-specific scFV, the α hinge and transmembrane portions from CD8, and the intracellular domain of CD3 zeta. P28, the other control species contains a P3MA-specific scFV and the intracellular, transmembrane and much of the extracellular portions of CD28. P28Z and PZ28 represent TCR's in accordance with the invention. In P28Z, the intracellular zeta chain portion is joined to the C-terminus of P28. In PZ28, the intracellular 41 amino acids (SEQ ID NO: 9) of CD28 are joined to the C-terminus of the PZ1 receptor.

The expansion of functional tumor-specific T lymphocytes is of central importance in tumor immunity. Whether in the context of in vivo immunization or ex vivo T-cell expansion, the biological requirements for T-cell priming and amplification have to be met to attain meaningful immune responses. Co-stimulation is crucial in this process 19-22 and is thus central to the development of effective adoptive immunotherapy of cancer 19,29.

The present invention describes chimeric TCRs and in particular scFv-based chimeric receptors designed to provide both TCR-like and co-stimulatory signals upon binding of the tumor antigen PSMA. To achieve this, the intracellular domains of human TCRζ and CD28 have been fused in series within a single molecule, thereby recruiting these signaling motifs to the site of antigen engagement at a fixed stoichiometry of 1:1. Most important, our study was performed in human primary T lymphocytes—that is, in biologically and therapeutically relevant cells. The ability to sustain T-cell expansion and tumoricidal functions could therefore be evaluated, which is not possible in leukemic cells 30,31. We show here that, following contact with cell-bound PSMA, activated human PBLs engineered to express the P28z receptor produce IL-2, undergo sequential rounds of expansion, and maintain thereafter their ability to execute specific lysis of PSMA-expressing target cells.

The most important finding in this study is the demonstration that expression of P28z enables T cells to undergo repeated rounds of antigen-dependent stimulation and expansion. This process was accompanied by a progressive increase in the proportion of transduced T cells within bulk cultures, consistent with the expected selective advantage conferred by the receptor. The capacity of P28z to deliver signal 1 is demonstrated by production of IL-2 and induction of cell proliferation upon stimulation with PSMA+B7.1, which are comparable to those obtained in T cells expressing Pz1 (which contains TCRζ but no CD28 sequences). Specific lysis of PSMA+ targets also reflects functional activation through the TCR pathway. Importantly, the P28z fusion receptor can also provide potent co-stimulation (signal 2). Thus, in the absence of exogenous B7-driven co-stimulation, engagement of PSMA elicits IL-2 production and proliferation. Under the same conditions, Pz1-transduced cells fail to secrete IL-2 and proliferate, corroborating findings by Finney et al. obtained in Jurkat cells 31.

The relative positions of the TCRζ and CD28 signaling elements within the fusion receptor proved crucial. In P28z, the hinge, transmembrane, and proximal intracellular portions of the molecule were derived from CD28, followed by the signaling domain of TCRζ. When CD28 sequences were fused to the C terminus of TCRζ, as in Pz28, the functional activity was substantially compromised relative to P28z, particularly with regard to sustaining proliferation. This occurred despite comparable cell-surface expression of the two receptors. Pz28 retained the ability to deliver a TCR-like signal upon PSMA binding, as evidenced by cytolytic activity and B7.1-dependent proliferation and IL-2 production. However the co-stimulatory potency of Pz28, as evaluated in the absence of B7.1, was no better than that of Pz1.

One potential explanation for this finding is that the conformational integrity of the fusion receptor is disrupted when the CD28 signaling domain is placed downstream of TCRζ. It is noteworthy in this regard that western blotting analysis indicated that the Pz28 receptor exhibited less homodimerization in human T cells than either P28z or Pz1. An alternative explanation is that membrane proximity is more critical for CD28 than for TCRζ. Thus, placement of the CD28 moiety distal to TCRζ might impair its ability to associate with downstream signaling molecules, such as p56-lck (ref. 32), which reside in very close proximity to the cell membrane. A third possibility is that these fusion receptors differ in their ability to interact with negative regulators, for example, MAP kinase phosphatase-6 (MKP-6) 33. It is plausible that the ability of P28z to bind MKP-6 might be impaired as a result of steric hindrance, thereby enhancing co-stimulatory activity. Conversely, in the case of Pz28, the binding of this phosphatase at the C terminus may adversely affect the signaling potency of this receptor. This hypothesis is supported by findings indicating that Pz28 was not only less active in eliciting IL-2 secretion than P28z, but also less active than Pz1. A final possible explanation for the superior function of P28z is that it contains the CD28 transmembrane domain, unlike Pz28 and Pz1. However, this is unlikely because the cytoplasmic portion of CD28 is sufficient for co-stimulatory activity 34.

How might adoptive transfer of cells expressing P28z be developed for therapy directed against PSMA-expressing tumors or tumor-associated vasculature? As this fusion receptor enables transduced T cells to proliferate in an antigen-dependent manner, this raises the prospect that these cells could be expanded both in vitro, before infusion, and, most importantly, in vivo in the tumor-bearing host. There is substantial preclinical evidence indicating that success of adoptive T-cell therapy depends largely on the relative numbers and growth kinetics of tumor cells and therapeutically administered T cells 35,36. Consequently, treatment with T cells expressing a receptor like P28z may require smaller T-cell doses (and thus shorter in vitro culture periods) and allow for T-cell expansion following infusion. As P28z-transduced T cells expanded on PSMA-positive cells retained their specific cytolytic activity, such a cell culture procedure could provide a useful means to selectively expand transduced T cells. Importantly, P28z provides a means to activate and expand T cells upon engaging cells that lack MHC and/or co-stimulatory molecules, and may thus target the transduced lymphocytes to cells that escape immune recognition.

In summary, we have shown that artificial receptors based upon fusion of the signaling domains of TCRζ and CD28 can be used to redirect the specificity of primary human T cells to a tumor antigen. The transduced T cells undergo selective expansion following contact with cell-bound PSMA while maintaining the ability to mediate specific lysis of tumor cells. The availability of a single chimeric receptor providing both activation and co-stimulatory functions facilitates lymphocyte transduction and hence clinical applicability.

Thus, the present invention also provides a method for stimulating a T cell mediated immune response to a target cell population in a subject individual comprising the step of administering to the subject individual a chimeric T cell receptor comprising a zeta chain portion comprising the intracellular domain of human CD3 ζ chain, a CD28 signaling region and a binding element that specifically interacts with a selected target such that the chimeric T cell receptor is expressed in T lymphocytes of the subject individual, wherein the binding element is selected to specifically recognize the target cell population.

As used in the specification and claims of this application, the term "administering" includes any method which is effective to result in expression of a chimeric TCR of the invention in T lymphocytes of the subject individual. One method for administering the chimeric TCR is therefore by ex vivo transduction of peripheral blood T cells or hematopoietic progenitor cells (which would eventually be allogeneic) with a nucleic acid construct in accordance with the invention and returning the transduced cells, preferably after expansion to the subject individual.

As used in the specification and claims of this application, the term "subject individual" refers to a living organism in which the immune response to the target cell population is to be induced. The subject individual is preferably mammalian, including humans, companion animals such as dogs and cats, horses, agricultural mammals such as cattle, pigs and sheep, and laboratory animals including mice and rats.

The invention will now be further described with reference to the following non-limiting examples.

Example 1 Recombinant receptors and retroviral vectors. All fusion receptors contain a scFv derived from the J591 hybridoma 25 as described[18]. To facilitate detection of transduced cells, all constructs contained the encephalomyocarditis Virus internal ribosome entry site (EMCV-IRES)[37] and the eGFP gene inserted in the SFG vector[38]. In Pz1, the J591 scFv is coupled through human CD8α hinge and transmembrane sequences to the intracellular domain of human TRCζ (ref. 18). P28 comprises a fusion of the J591 scFv to human CD28 as described[23,39]. To construct P28z, nucleotides 336-660 of CD28 were amplified using primers 5'-GGCGGCCG CAAT-TGAAGTTATGTATC-3' (SEQ. ID NO: 4) and 5'-TGCGCTCCTGCTGAACTTCACTCTG-GAGCGATAGGCTGCTAAGTCGCG-3 SEQ ID NO: 5). The intracellular domain of TCRζ was amplified using primers 5'-AGAGTGAAGTTCAGCAGGAGCGCA-3' (SEQ. ID NO: 1) and 5'-CTCGAGTGGCTGTTAGCCAGA-3' (SEQ ID NO: 2). The products were fused in a separate PCR reaction driven by primers of SEQ ID Nos. 4 and 2, A-tailed with Taq polymerase, and subcloned as a NotI/XhoI ligament into SFG-Pz1. To generate Pz28, the intracellular domain of CD28 was amplified using 5'-GCACTTCACATGCAGGC TCTGCC<u>A</u>CCTCGCAGGAGTAAGAGGAGCAGG CTC-CTGCAC-3' (SEQ ID NO: 7)and 5'-CGCTCGAGTCAG-GAGCGATAGGCTGCGAAGTCGCGT-3' (SEQ ID NO: 8) (two silent mutations introduced to interrupt cytosine repeats are underlined). The resultant PCR product represents a fusion of the distal nine codons of TCRζ (minus stop codon) to the intracellular domain of CD28 and contains a convenient 5' NspI site. This fragment was subcloned, digested with NspI/XhoI, and ligated into SFG-Pz1. SFG-c-fms encodes the human macrophage colony-stimulating factor receptor. This resulted in a series of receptors that comprise a PSMA-specific scFv fragment coupled to signaling elements derived from TCRζ and/or CD28 (FIG. 2). Pz118 and P28 are designed to respectively deliver signals 1 and 2 in a PSMA-dependent manner. In P28z, the intracellular portion of TCRζ has been joined to the C terminus of P2823, while in Pz28, the CD28 signaling domain was added at the C terminus of Pz1. All chimeric complementary DNAs (cDNAs) were cloned in bicistronic onco-retroviral vectors upstream of enhanced green fluorescent protein (eGFP; FIG. 1).

Example 2 Culture and retroviral transduction of primary human T cells. Peripheral blood mononuclear cells from healthy donors were established in RPMI+10% (vol/vol) human serum, activated with phytohemagglutinin (2 µg/ml) for two days, and transferred to non-tissue culture-treated plates (FALCON, Becton Dickinson, Franklin Lakes, N.J.) precoated with retronectin (15 µg/ml; Takara Biomedicals, Shiga, Japan). Gibbon ape leukemia virus envelope-pseudotyped retroviral particles were generated as described[27,40]. Transduced cells were co-cultivated with NIH3T3 fibroblasts expressing PSMA and/or B7.1 as described[18,23]. For experiments with LNCaP cells, cells were admixed weekly at a T-cell: tumor cell ration of 5:1.

For protein analyses, flow cytometry was carried out using a FACScan cytometer with Cellquest software. Expression of PSMA-specific fusion receptors was directly demonstrated using phycoerythrin (PE)-conjugated goat anti-mouse antiserum 18. CD4-PE and CD8-PerCP antibodies (Becton Dickinson) were used for T-cell subset identification. For western blot analysis, transduced T-cell samples were prepared as described 41. Briefly, cells were suspended in radioimmunoprecipitation buffer at a concentration of 1×10-7 cells/ml. After 1 hour incubation on ice, cells were boiled in 2× loading buffer under nonreducing or reducing conditions with 0.1 M dithiothreitol. Samples were run on 10-20% acrylamide gradient gels and transferred to polyvinylidene fluoride transfer membrane (NEN Life Science Products, Boston, Mass.). Fusion proteins were detected using the anti-human ζ-chain monoclonal antibody 8D3 (PharMingen, San Diego, Calif.) as described 41. Immunodetection was performed using the ECL Plus western blotting detection system (Amersham, Buckinghamshire, UK).

Three days after transduction of mitogen-activated PBLs, gene transfer efficiency, as assessed by flow cytometry, ranged from 20% to 70%. CD4+ and CD8+ T-cells subsets were transduced at similar efficiencies, as reported elsewhere 18,19,27. Expression of ζ-chain containing fusion receptors was also analyzed by western blotting, confirming homodimer formation and little, if any, heterodimerization with endogenous CD8 or CD28.

To determine the percentage transduction of T-cell subsets, samples were also stained with CD4 PE and CD8 PerCP antibodies and analyzed by three-color flow cytometry, using GFP emission to identify transduced cells. Quadrants were set using control samples so that 99% of events were negative for the marker of interest. Surface expressions of Pz1 was typically greater than that of P28 or either of the TCR ζ-CD28 fusion receptors. Mean fluorescence intensity when Pz1 expression was normalized to 100 was as follows: P28=35.1∀17.8 ($P<0.05$); P28z=29.6∀12.2 ($P<0.01$);

Pz28=25.9∀6.9 (P<0.01) (n=3-4 experiments). There was no significant difference in expression intensity between P28, P28z, Pz28.

Lysates were prepared under reducing and nonreducing conditions from PBLs following transduction with Pz1 (54% GFP-expressing), P28z (21% GFP-expressing), and Pz28 (20% GFP-expressing). Untransduced PBLs were used as controls. Immunoreactive receptor hands were detected by western blotting using an anti-TCRζ monoclonal antibody. Filled arrows indicate the monomeric and dimeric forms of the endogenous TCRζ. Pz1 and Pz28 are predominantly expressed as homedimers, as would be expected from the design of the hinge regions of these molecules. However, Pz28 was found to dimeric less effectively in T-cells and in PG13 cells (data not shown). No hands indicating productive heterodimerization with CD8α, CD8β or CD28 were detected. The additional hand seen under that corresponding to dimerized ζ is likely to be a degradation product of this dimer. Empty arrows show the positions of the monomeric and dimeric PSMA-specific fusion receptors. Molecular mass markers are indicated on the left on the panel.

Example 3 Cytotoxicity assays. Cytotoxic T-lymphocyte assays were performed using a nonradioactive cytotoxicity detection kit (lactate dehydrogenase (LDH); Roche Diagnostics, Indianapolis, Ind.) as described 18.

Figure 3A:
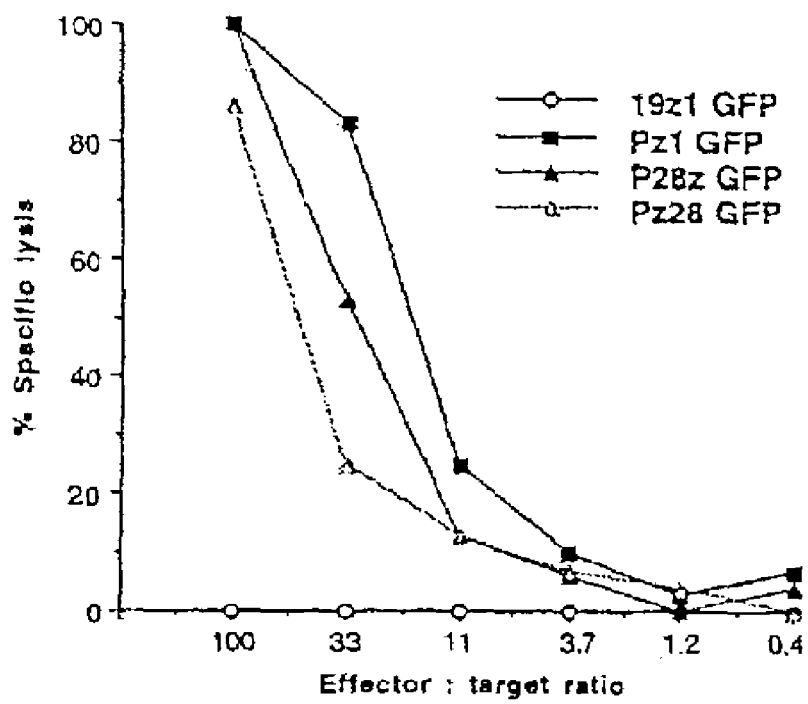
FIGS. 3 A and B show specific target lysis by PSMA redirected T cells.

To confirm that the TCRζ-CD28 fusion receptors specifically engaged PSMA, cytotoxicity assays were performed three days after the transduction. T-cells were transduced with 19z1GFP (control), Pz1 GFP, or Pz28 GFP. Three days after completion of gene transfer 4 h CTL assays were established at the indicated ratios using as targets NIH3T3 cells expressing PSMA. No specific lysis was observed using untransduced NIH3T3 as control targets. The greater lytic activity of Pz1-transduced cells may reflect the higher cell-surface expression of this receptor, or, more likely, the greater proportion of transduced T-cells (46% of T-cells, of which 21% are CD8+, compared with 25% P28z-transduced cells, including 12% CD8, and 20% Pz28-transduced cells, including 10% CD8+ cells). The control 19z1 receptor (specific for CD19) did not effect lysis of PSMA expressing targets, despite the presence of the same TCRζ chain in this molecule. Both P28z and Pz28 receptors, but not P28, mediated specific lysis of fibroblasts expressing human PSMA (FIG. 3A).

Example 4 P28z-transduced T-cells were stimulated on NIH3T3 cells expressing PSMA and, after one week, were established in 4 h CTL assays with NIH3T3 cells expressing PSMA or untransduced cells as controls. At this time, the T-cells were 62% GFP+ (of which 17% were CD8+). (FIG. 3B) The fusion receptor P28z elicits IL-2 production upon engagement with PSMA. To assay the ability of the different receptors to signal for IL-2 production, transduced PBLs were co-cultivated with NIH3T3 cells expression PSMA and/or B7.1 (refs 18,19) in medium lacking IL-2 (Table 1). Three receptors (Pz1, P28z, and Pz28) elicited IL-2 secretion in the presence of the PSMA and B7.1. In the absence of the co-stimulatory ligand, IL-2 production was only observed in cultures of P28z-transduced T-cells. IL-2 levels were elated, ranging within 40-55% of those obtained by co-culturing the same transduced T-cells with the monolayer co-expressing PSMA and B7.1.

Figure 3B:
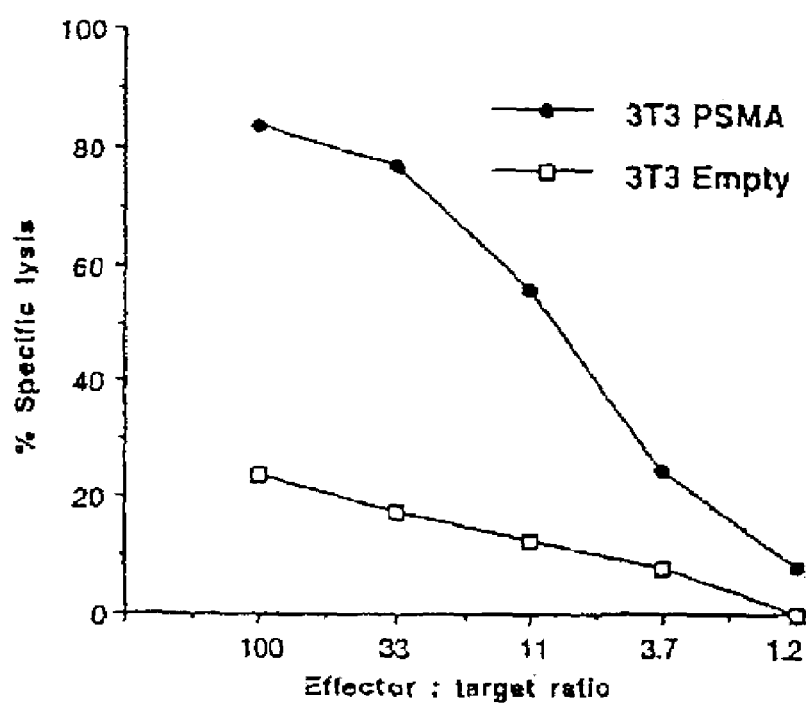
Figure 4A:
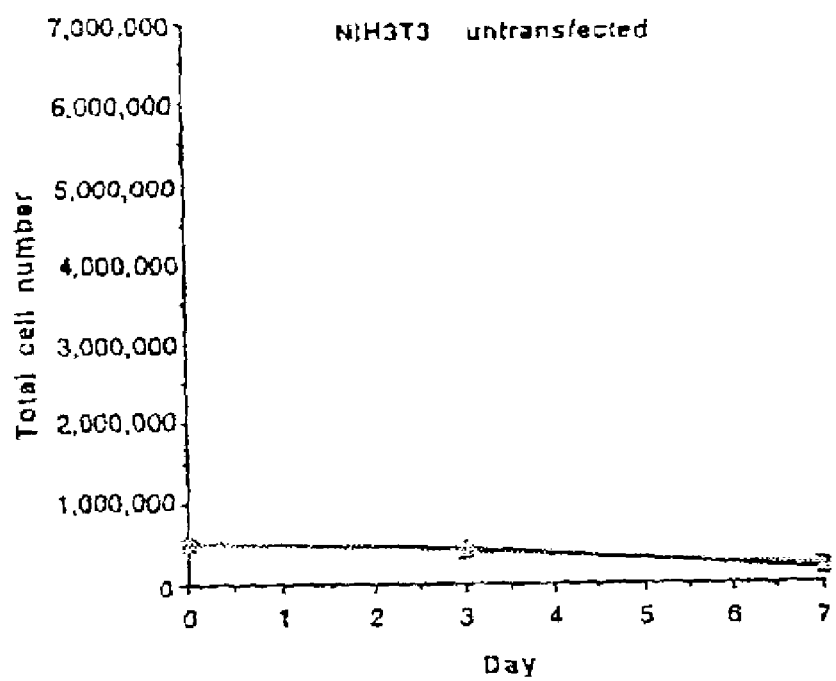
FIGS. 4 A-D. The P28z fusion receptor renders human T lymphocytes capable of PSMA-dependent expansion. Human T cells were transduced with the following retroviral constructs (gene transfer efficiency indicated in parentheses): SFG 19z1 (60%), SFG P28 (53%), SFG PZ1 (68%), SFG P28z (23%), and SFG Pz28 (32%). Three days later, 5×105 transduced T cells were co-cultured in 20 U/ml IL-2 with irradiated NIH3T3 feeder cells as follows: (A) unmodified (B) NIH3T3-B7.1 (C) NIH3T3-PSMA, or (D) NIH3T3-PSMA+B7.1. Cell numbers were counted on days 3 and 7, and data presented are mean±s.d. of triplicate evaluations. Similar results were obtained in three experiments.
Figure 4B:
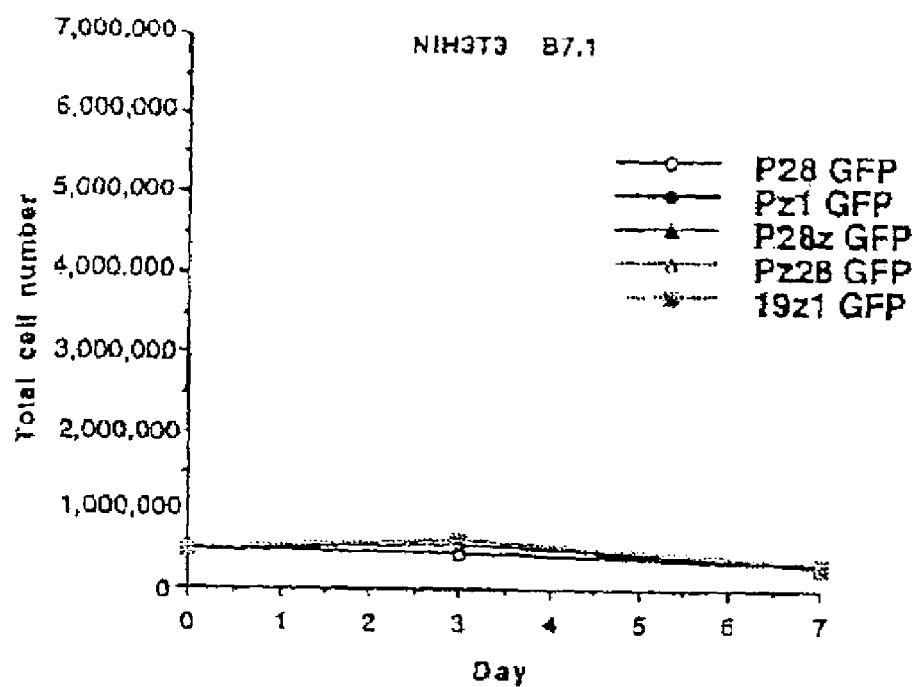
Figure 4C:
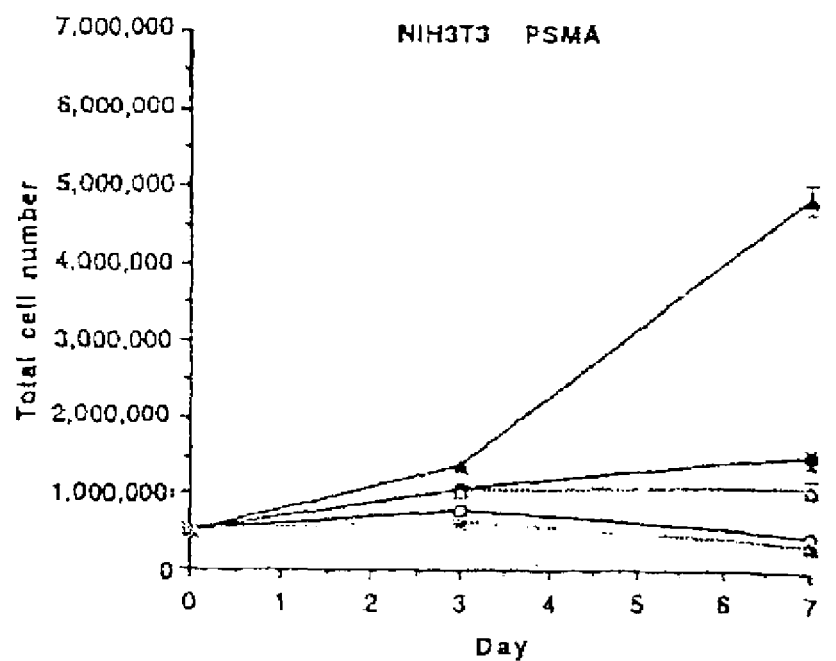
Figure 4D:
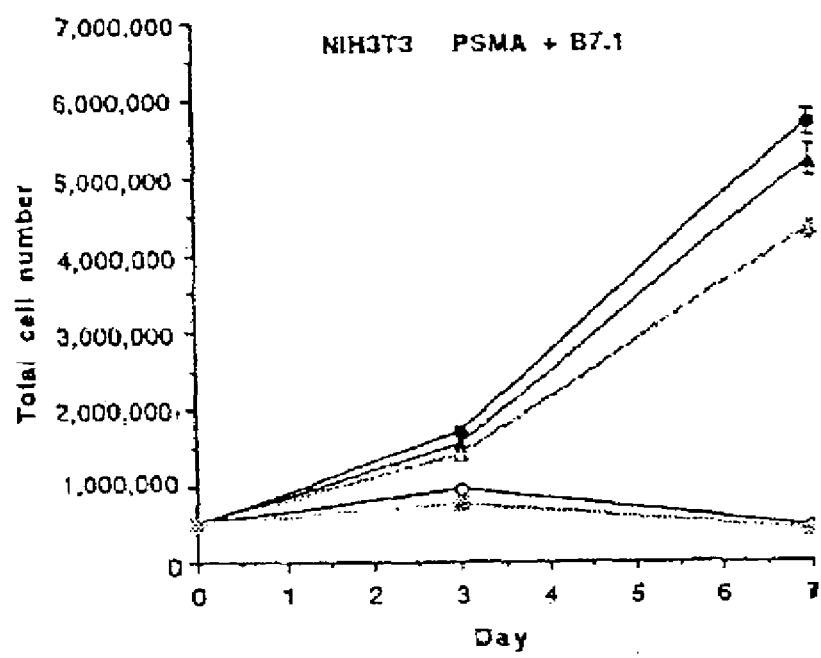

The P28z fusion receptor promotes proliferation of genetically modified T-cells in response to PSMA. To test if P28z could deliver combined and functional signals 1 and 2, transduced PBLs were plated on NIH3T3 cells expressing B7.1, PSMA, PSMA+B7.1, or on unmodified NIH3T3 cells. All cultures declined over one week in the absence of PSMA (FIG. 4A, B). When stimulated by a monolayer co-expressing PSMA+B7.1 (FIG. 4D), Pz1-transduced PBLs underwent expansion, as did PBLs transduced with P28z or Pz28, further establishing that both TCRζ CD28 fusion receptors deliver a TCR-like signal. Control P28-transduced T cells did not expand under these conditions, indicating that neither co-stimulation alone nor adherence to the monolayer enhanced proliferation. When stimulation was provided by NIH3T3 cells expressing PSMA alone (FIG. 4C), T-cells expressing Pz1 underwent limited expansion. Pz28-transduced cells also (grew poorly, further indicating that this fusion receptor does not deliver a meaningful co-stimulatory signal. By contrast, P28z-transduced T-cells consistently proliferated, corroborating observation by Eshhar et al. showing that immobilized hapten can induce proliferation in T-cells that express a trinitophenol-specific CD28-Fcγ fusion receptor 28. P28z-transduced T-cells markedly expanded, showing absolute increases in cell numbers 8.6±5.2-fold over a seven-day period, n=8 experiments). Taken together, these data strengthen the argument that P28z can provide both signals 1 and 2. Importantly, after seven days of co-culture onto a PSMA+ fibroblast monolayer, T-cells expressing the P28z fusion receptor retained the ability to specifically lyse PSMA+ targets (FIG. 3B).

Figure 5A:
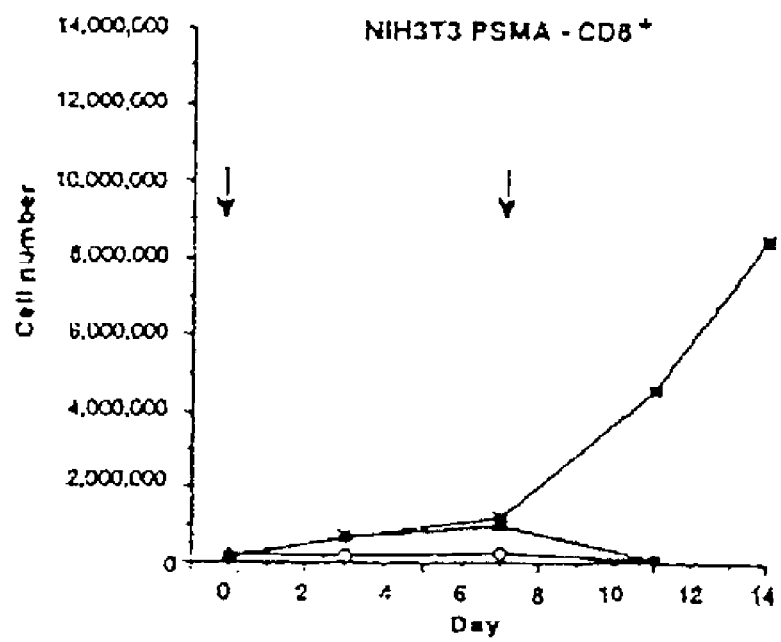
FIGS. 5 A-F. Primary and secondary stimulation of transduced T cells in response to PSMA. Peripheral blood T cells were transduced with the following retroviral constructs (gene transfer efficiency indicated in parentheses); P28 (27%), Pz1 (36%), or P28z (17%). Then the cells were subjected to two rounds of stimulation on NIH3T3 fibroblast feeder layers (indicated by arrows). For the primary stimulation, 1×106 transduced T cells were co-cultured in IL-2 (20 U/ml) with irradiated NIH3T3 cells expressing PSMA (panels A and B) or PSMA+B7.1 (panels C and D). On day 7, cultures were re-stimulated by co-culture with a similar monolayer. Absolute numbers of transduced CD8+ (panels A and C) and CD4+ T cells (panels B and D) were calculated as the product of percentage transduced (determined by flow cytometry)×total cell count. Co-culture of all transduced PBL populations with B7.1 expressing or unmodified NIH3T3 cells resulted in a progressive decline in total cell number and content of transduced T cells (data not shown). (E) P28z-transduced T cells were expanded by sequential re-stimulation on NIH3T3 PSMA fibroblast feeder layers, is indicated by the arrows. Cultures were maintained in IL-2 (20 U/ml), which was added every three days. The data represent the mean±s.d. of six data points (triplicate cell counts from two separate cultures). These cultures were subjected to three-color flow cytometry at intervals to detect transduced (eGFP+) cells of the CD4+ and CD8+ subsets. Similar data were obtained upon analysis of both cultures, and data shown are from one representative example (F).
Figure 5B:
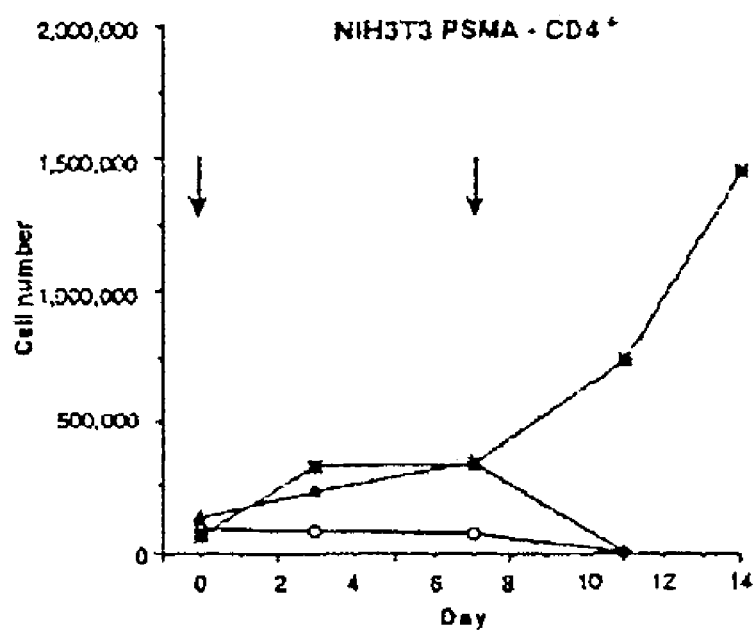
Figure 5C:
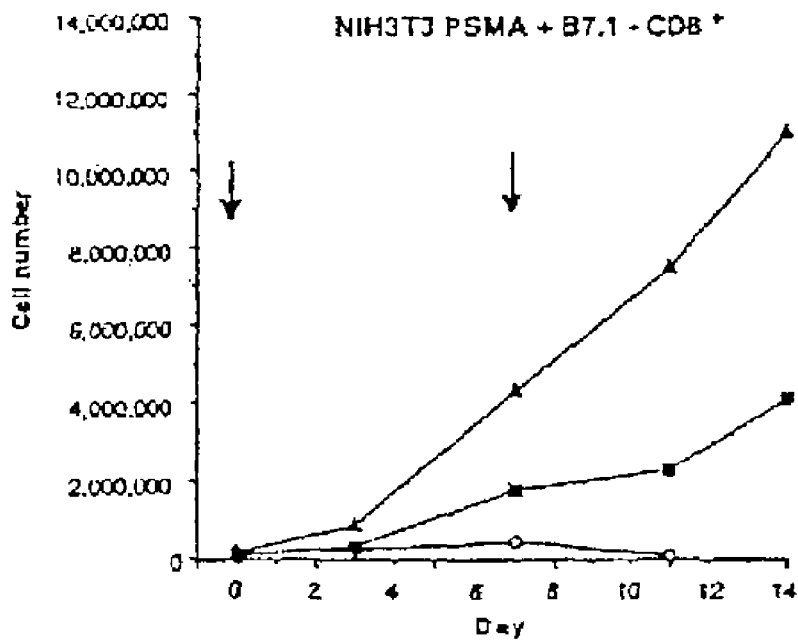
Figure 5D:
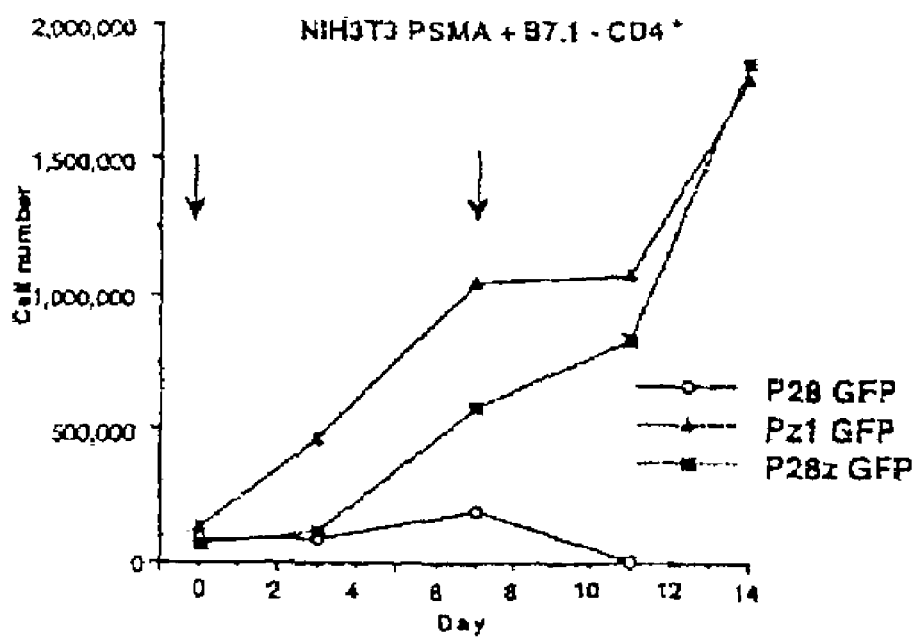
Figure 5E:
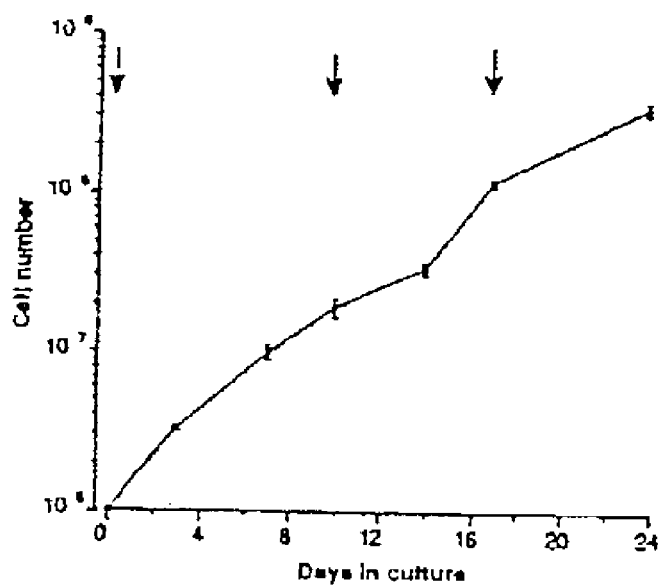
Figure 5F:
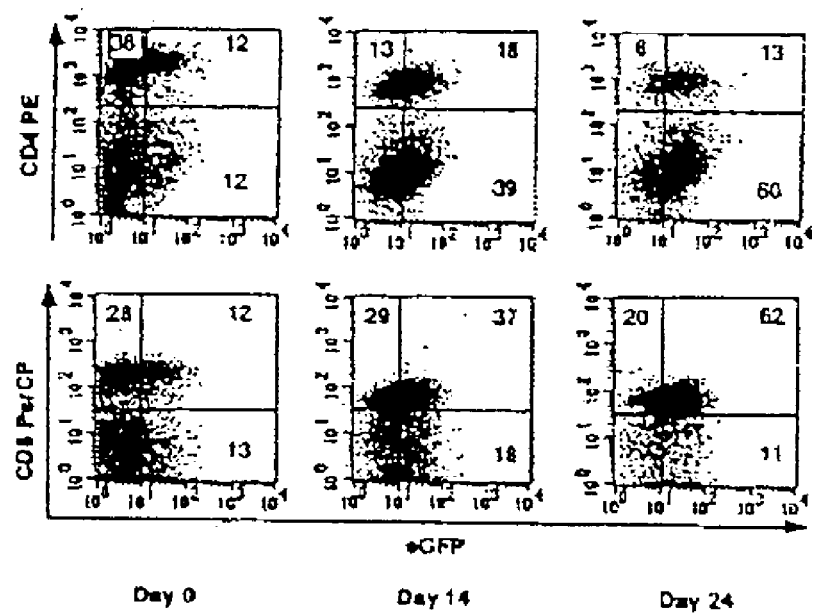

Example 5 The P28z fusion receptor permits sequential re-stimulation of transduced human PBLs in response to PSMA. If P28z can provide co-stimulation in addition to a TCR like signal, it would be expected that cells expressing the receptor should undergo further expansion upon secondary encounter with PSMA. However, if the co-stimulatory potency of this molecule is inadequate, sequential exposure to antigen could result in a poor proliferative response resulting from induction of energy and/or apoptosis[20,21]. To test this, transduced PBLs stimulated on the different NIH3T3 manslayers were subjected to secondary re-stimulation after a seven-day interval. Pz1 transduced T-cells expanded in response to primary encounter with PSMA. However, re-stimulation with PSMA resulted in a dramatic decline in the number of transduced cells (FIG. 5A, B). Importantly, the same T-cells underwent brisk expansion after both primary and secondary stimulation if the fibroblast manslayer co-expressed PUMA and B7.1 (FIGS. 5C and D, respectively). In contrast, the absolute number of P28z-transduced CD8+ and CD4+ T cells increased after primary stimulation and underwent further increase after re-stimulation on day 7, irrespective of the presence of B7.1. Expansion was indeed similar in response to PSMA alone or PSMA+B7.1, underscoring the relative potency of the co-stimulatory signal provided by P28z. Re-stimulation of P28z cultures with PSMA yielded a 4.0±2.4-fold expansion in total cell number over a seven-day period (n=4 experiments). Following another re-stimulation under the same conditions, the total cell number increased by more than 2 logs over a three-week interval (FIG. 5E). In this period, a progressive enrichment of transduced over non-transduced cells was observed, in keeping with the selective advantage conferred to cells expressing p28z. (FIG. 5F). Together, these data provide conclusive evidence that P28z delivers a functional signal 1 and 2 upon interaction with PSMA. Importantly, the same result was obtained with another receptor, 19-28z, which was modeled on P28z, 19-28z-transduced PBLs showed the same ability to be re-stimulated by CD19+ cells and to proliferate, indicating that proliferative responses were achieved with receptors recognizing unrelated antigens.

Figure 6A:
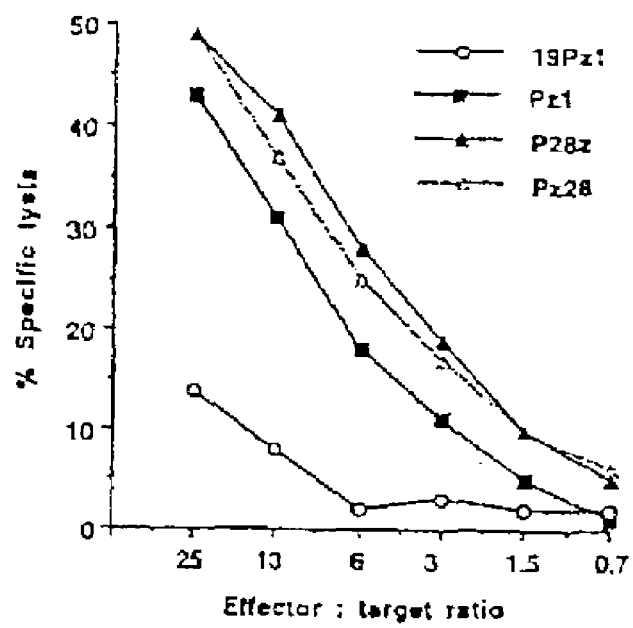
FIGS. 6A and B. PSMA+ tumor cells activate cytolytic and proliferative responses in P28z-transduced PBLs. (A) Specific tumor cell lysis by PSMA-redirected T cells. T cells were transduced with 19z1 (control), Pz1, P28z GFP, and Pz28 GFP. Four days after completion of gene transfer, equivalent numbers of transduced T cells were added to LNCaP human prostate cells. All PSMA-specific T cells (Pz1, P28z, and Pz28) demonstrated cytotoxic activity similar to that demonstrated against NIH3T3 PSMA+ fibroblasts. Background cytotoxic activity seen with 19z1 control T cells may be due to alloreactivity (which is not seen with the murine NIH3T3 fibroblasts.
Figure 6B:
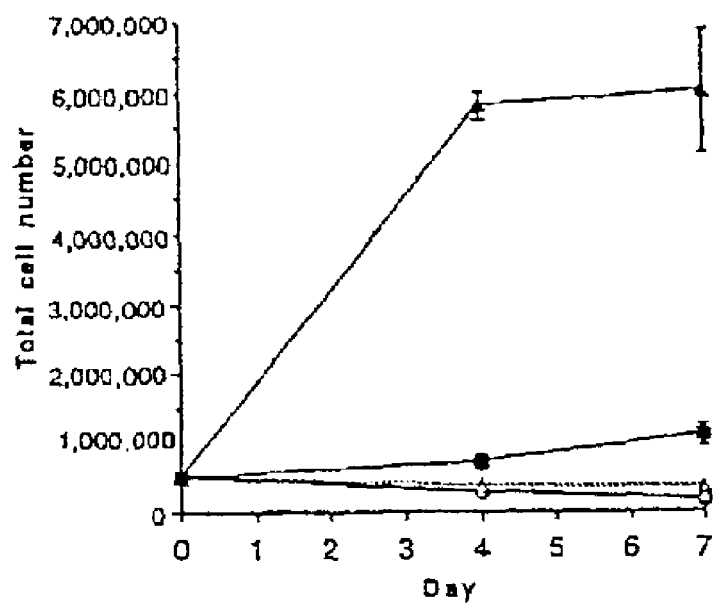

Example 6 P28z-transduced PBLs lyse PSMA+ tumor cells and proliferate in response to LNCaP cells. We had previously shown that Pz1-transduced T cells specifically lyse LNCaP cells, a PSMA+ human prostate cancer cell line, as well as PSMA-transduced PC3 and EL4 cells, which are respectively a human prostate cancer cell line and a murine thymoma 19. Pz1, P28z, and Pz28 directed comparable and elevated cytolytic activity against LNCaP cells (FIG. 6A). Proliferative responses elicited by LNCaP cells expressing B7.1 were also comparable for these receptors (data not shown). Of the three receptors, however, only P28z could induce sustained proliferation during co-cultivation with LNCaP cells (FIG. 6B). The re-stimulated T cells preserved their tumoricidal activity (data not shown), corroborating findings obtained with PSMA+ fibroblasts (FIG. 3B).

Example 7 To construct a CD19-specific scFv, we cloned the heavy (VH) and light (VL) chain variable regions from hybridoma cell line SJ25C1 derived cDNA by the polymerase chain reaction (PCR) using degenerate primers described by Orlandi et. al.[43] and fused these coding regions with a DNA fragment encoding for a (Gly3Ser)$_4$ spacer region. We ligated a costimulatory signaling element from human CD28, including transmembrane and extracellular portions SEQ ID NO: 6) to the 3' end of the resulting scFv and the cytoplasmic domain of the human-ζ SEQ ID NO: 3) to the 3' end of the CD28 portion to form fusion gene 19-28z.

The 19-28z fusion was tested for its ability to reduce tumor growth and enhance survival in mice injected with NALM6 T cells. NALM6 cells express CD19, MHC I, and MHC II but not B7.1 or B7.2. Most (~80%) untreated SCID-Beige mice develop hind-limb paralysis 4-5 weeks after tumor cell injection, remaining mice develop weight loss and/or other CNS symptoms (i.e. vestibular symptoms). When the 18-28z fusion was present, T cell stimulation was enhanced nearly ten-fold, and survival of some of the mice was greatly extended as compared to mice treated with Pz1 (a PSMA specific construct) or 19z1, a CD19-specific construct lacking the costimulatory signaling element.

Example 8 A chimeric TCR containing a CD19 binding element, 4-1BB as the costimulatory region and the intracellular domain of the CD3ζ chain in that order is prepared using the methodology of Example 1. The 4-1BB is amplified using the following primers GCGGCCGCA-CCATCTCCAGC-CGAC SEQ ID NO: 18) and CTTCACTCT-CAGTTCA-CATCCTTC SEQ ID NO: 19) to generate a 4-1BB amplicon with CD19 scFv and zeta tails with restriction cleavage sites to facilitate ligation to the CD19 scFv and zeta chain portions. The hyphen in the sequence indicates the transition from the 4-1BB sequence to the tail. The same primer can be used for other binding elements such as PSMA which end in the same sequence.

Example 9 A chimeric TCR containing a CD19 binding element, ICOS as the costimulatory region and the intracellular domain of the CD3 ζ chain in that order is prepared using the methodology of Example 1. The ICOS is amplified using the following primers GCGGCCGCA-CTAT-CAATTTTTGATCCT SEQ ID NO: 20) and CTTCACTCT-TAGGGTCACATCTGTGAG SEQ ID NO: 21) to generate a ICOS amplicon with CD19 scFv and zeta tails with restriction cleavage sites to facilitate ligation to the CD19 scFv and zeta chain portions. The hyphen in the sequence indicates the transition from the ICOS sequence to the tail. The same primer can be used for other binding elements such as PSMA which end in the same sequence.

Example 10 A chimeric TCR containing CD19 binding element, DAP-10 as the costimulatory region and the intracellular domain of the CD3 ζ chain in that order is prepared using the methodology of Example 1. The DAP-10 is amplified using the following primers GCGGCCGCA-CAGAC-GACCCCAGGA (SEQ ID NO: 22) and CTTCACTCT-GC-CCCTGCCTGGCATG (SEQ ID NO: 23) to generate a DAP-10 amplicon with CD19 scFv and zeta tails with restriction cleavage sites to facilitate ligation to the CD19 scFv and zeta chain portions. The hyphen in the sequence indicates the transition from the DAP-10 sequence to the tail. The same primer can be used for other binding elements such as PSMA which end in the same sequence.

The following references are cited herein and are incorporated herein by reference.

1. Gilboa, E. How tumors escape immune destruction and what we can do about it. Cancer Immunol. Immunother. 48, 382-385 (1999).
2. Melief, C. J. et al. Strategies for immunotherapy of cancer. Adv. Immunol. 75, 235-282 (2000).
3. Ferrone, S., Finerty, J. F., Jaffee, E. M. & Nabel, G. J. How much longer will tumor cells fool the immune system. Immunol. Today 21, 70-72 (2000).
4. Houghton, A. N. Cancer antigens: immune recognition of self and altered self. J. Exp. Med. 180, 1-4 (1994).
5. Boon, T., Coulie, P. D. & Van den Eynde, B. Tumor antigens recognized by T cells. Immunol. Today 18, 267-268 (1997).
6. Nanda, N. K. & Sercarz, E. E. Induction of anti-self-immunity to cure cancer. Cell 82, 13-17 (1995).
7. Sotomayor, E. M., Borrello, I. & Levitsky, H. I. Tolerance and cancer: a critical issue in tumor immunology. Crit. Rev. Oncog. 7, 433-456 (1996).
8. Kiertscher, S. M., Luo, J., Dubinett, S. M. & Roth, M. D. Tumors promote altered maturation and early apoptosis of monocyte-derived dendritic cells. J. Immunol. 164, 1269-1276 (2000).
9. Almand, B. et al. Increased production of immature myeloid cells in cancer patients: a mechanism of immunosuppression in cancer. J. Immunol. 166, 678-689 (2001).
10. Lee, P. P. et al. Characterization of circulating T cells specific for tumor-associated antigens in melanoma patients. Nat. Med. 5, 677-685 (1999).
11. Marincola, F. M., Jaffee, E. M., Hicklin, D. J. & Ferrone, S. Escape of human solid tumors from T cell recognition: molecular mechanisms and functional significance. Adv. Immunol. 74, 181-273 (2000).
12. Eshhar, Z., Waks, T., Gross, G. & Schindler, D. G. Specific activation and targeting of cytotoxic lymphocytes through chimeric single chains consisting of antibody-binding domains and the gamma or zeta subunits of the immunoglobulin and T-cell receptors. Proc. Natl. Acad. Sci. USA 90, 720-724 (1993).
13. Altenschmidt, U., Moritz, D. & Groner, B. Specific cytotoxic T lymphocytes in gene therapy. J. Mol. Med. 75, 259-266 (1997).
14. Paillard, F. Immunotherapy with T cells bearing chimeric antitumor receptors. Hum. Gene Ther. 10, 151-153 (1999).
15. Geiger, T. L., Leitenberg, D. & Flavell, R. A. The TCRζ-chain immunoreceptor tyrosine-based activation motifs are sufficient for the activation and differentiation of primary T lymphocytes. J. Immunol. 162, 5931-5939 (1999).
16. Haynes, N. M. et al. Redirecting mouse CTL against colon carcinoma: superior signaling efficacy of single-chain variable domain chimeras containing TCR-ζ vs FcRI-γ. J. Immunol. 166, 182-187 (2001).
17. Whiteside, T. L. Signaling defects in T lymphocytes of patients with malignancy. Cancer Immunol. Immunother. 48, 346-352 (1999).
18. Gong, M. C. et al. Cancer patient T cells genetically targeted to prostate-specific membrane antigen specifically lyse prostate cancer cells and release cytokines in response to prostate-specific membrane antigen. Neoplasia 1, 123-127 (1999).

19. Harding, F. A., McArthur, J. G., Gross, J. A., Raulet, D. H. & Allison, J. P. CD28-mediated signaling co-stimulates murine T cells and prevents induction of anergy in T cell clones. Nature 356, 607-609 (1992).
20. Lenschow, D. J., Walanus, T. L. & Bluestone, J. A. CD28/B7 system of T cell co-stimulation. Annu. Rev. Immunol. 14, 233-258 (1996).
21. Ward, S. G. CD28: a signaling perspective. Biochem. J. 318, 361-377 (1996).
22. Greenfield, E. A., Nguyen, K. A. & Kuchroo, V. K. CD28/B7 co-stimulation: a review. Crit. Rev. Immunol. 18, 389-418 (1998).
23. Krause, A. et al. Antigen-dependent CD28 signaling selectively enhances survival and proliferation in genetically modified activated human primary T lymphocytes. J. Exp. Med. 188, 619-626 (1998).
24. Israeli, R. S., Powell, C. T., Corr, J. G., Fair, W. R. & Heston, W. D. W. Expression of the prostate-specific membrane antigen. Cancer Res. 54, 1807-1811 (1994).
25. Liu, H. et al. Monoclonal antibodies to the extracellular domain of prostate-specific membrane antigen also react with tumor vascular endothelium. Cancer Res. 57, 3629-3634 (1997).
26. Gong, M. C., Chang, S. S., Sadelain, M., Bander, N. H. & Heston, W. D. W. Prostate-specific membrane antigen (PSMA)-specific monoclonal antibodies in the treatment of prostate and other cancers. Cancer Metastasis Rev. 18, 483-490 (1999).
27. Gallardo, H. F., Tan, C., Ory, D. & Sadelain, M. Recombinant retroviruses pseudotyped with the vesicular stomatitis virus G glycoprotein mediate both stable gene transfer and pseudotransduction in human peripheral blood lymphocytes. Blood 90, 952-957 (1997).
28. Eshhar, Z., Waks, T., Bendavid, A. & Schindler, D. G. Functional expression of chimeric receptor genes in human T cells. J. Immunol. Meth. 248, 67-76 (2001).
29. Liebowitz, D. N., Lee, K. P. & June, C. H. Co-stimulatory approaches to adoptive immunotherapy. Curr. Opin. Oncol. 10, 533-541 (1998).
30. Alvarez-Vallina, L. & Hawkins, R. E. Antigen-specific targeting of CD28-mediated T cell co-stimulation using chimeric single-chain antibody variable fragment-CD28 receptors. Eur. J. Immunol. 26, 2304-2309 (1996).
31. Finney, H. M., Lawson, A. D. G., Bebbington, C. R. & Weir, A. N. C. Chimeric receptors providing both primary and co-stimulatory signaling in T cells from a single gene product. J. Immunol. 16, 2791-2797 (1998).
32. King, P. D., et al. Analysis of CD28 cytoplasmic tail tyrosine residues as regulators and substrates from the protein tyrosine kinases, EMT and LCK. J. Immunol. 158, 580-590 (1997).
33. Marti, F. et al. Negative-feedback regulation of CD28 co-stimulation by a novel mitogen-activated protein kinase phosphatase, MKP6. J. Immunol. 166, 197-206 (2001).
34. Stein, P. H., Fraser, J. D. & Weiss, A. The cytoplasmic domain of CD28 is both necessary and sufficient for co-stimulation of interleukin-2 secretion and association with phosphatidylinositol 3'-kinase. Mol. Cell. Biol. 14, 3392-3402 (1994).
35. Hanson, H. L. et al. Eradication of established tumors by CD8+ T cell adoptive immunotherapy. Immunity 13, 265-276 (2000).
36. Cordaro, T. A. et al. Tumor size at the time of adoptive transfer determines whether tumor rejection occurs. Eur. J. Immunol. 30, 1297-1307 (2000).
37. Gallardo, H. F., Tan, C. & Sadelain, M. The internal ribosome entry site of the encephalomyocarditis virus enables reliable co-expression of two transgenes in primary human T lymphocytes. Gene Ter. 4, 1115-1119 (1997).
38. Rivière, I., Brose, K. & Mulligan, R. C. Effects of retroviral vector design on expression of human adenosine deaminase in murine bone marrow transplant recipients engrafted with genetically modified cells. Pros. Natl. Acad. Sci. USA 92, 6733-6737 (1995).
39. Krause, A., Gong, M., Tan, C. & Sadelain, M. Genetic approaches to sustain the function of tumor-specific T-lymphocytes. Mol. Ther. 1, S260, 713 (2000).
40. Rivière, I., Gallardo, H. F., Hagani, A. B. & Sadelain, M. Retroviral-mediated gene transfer in primary murine and human T-lymphocytes. Mol. Biotechnol. 15, 133-142 (2000).
41. Jensen, M. C. et al. Human T lymphocyte genetic modification with naked DNA. Mol. Ther. 1, 49-55 (2000).
42. Vukmanovic-Stejic, M., Vyas, B., Gorak-Stolinska, P., Noble, A. & Kemeny, D. M. Human Tc1 and Tc2/Tc0 CD8 T cell clones display distinct cell surface and functional phenotypes. Blood 95, 231-240 (2000).
43. Orlandi R, Gussow D H, Jones P T, Winter G. Cloning immunoglobulin variable domains for expression by the polymerase chain reaction. Proc Natl Acad Sci USA. 1989; 86:3833-3837.

SEQUENCE LISTING

<160> NUMBER OF SEQ ID NOS: 23
<210> SEQ ID NO 1
<211> LENGTH: 24
<212> TYPE: DNA
<213> ORGANISM: human

<400> SEQUENCE: 1
agagtgaagt tcagcaggag cgca                                           24

<210> SEQ ID NO 2
<211> LENGTH: 21
<212> TYPE: DNA
<213> ORGANISM: human

```
<400> SEQUENCE: 2
ctcgagtggc tgttagcgag g                                               21

<210> SEQ ID NO 3
<211> LENGTH: 336
<212> TYPE: DNA
<213> ORGANISM: human

<400> SEQUENCE: 3
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 4
<211> LENGTH: 25
<212> TYPE: DNA
<213> ORGANISM: human

<400> SEQUENCE: 4
ggcggccgca atgaagttat gtatc                                           25

<210> SEQ ID NO 5
<211> LENGTH: 48
<212> TYPE: DNA
<213> ORGANISM: human

<400> SEQUENCE: 5
tgcgctcctg ctgaacttca ctctggagcg ataggctgcg aagtcgcg                  48

<210> SEQ ID NO 6
<211> LENGTH: 328
<212> TYPE: DNA
<213> ORGANISM: human

<400> SEQUENCE: 6
caaaattgaa gttatgtatc ctcctcctta cctagacaat gagaagagca atggaaccat     60
tatccatgtg aaagggaaac acctttgtcc aagtccccta tttcccggac cttctaagcc    120
cttttgggtg ctggtggtgg ttggtggagt cctggccttg ctatagcttg ctagtaacagt   180 ggcctttatt attttctggg tgaggagtaa gaggagcagg ctcctgcaca gtgactacat    240
gaacatgact ccccgccgcc ccgggcccac ccgcaagcat taccagccct atgccccacc    300
acgcgacttc gcagcctatc gctcctga                                       328

<210> SEQ ID NO 7
<211> LENGTH: 57
<212> TYPE: DNA
<213> ORGANISM: human

<400> SEQUENCE: 7
gcacttcaca tgcaggctct gccacctcgc aggagtaaga ggagcaggct cctgcac        57

<210> SEQ ID NO 8
<211> LENGTH: 36
<212> TYPE: DNA
<213> ORGANISM: human
```

<400> SEQUENCE: 8
cgctcgagtc aggagcgata ggctgcgaag tcgcgt                                    36

<210> SEQ ID NO 9
<211> LENGTH: 41
<212> TYPE: PRT
<213> ORGANISM: human

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 10
<211> LENGTH: 220
<212> TYPE: PRT
<213> ORGANISM: human

<400> SEQUENCE: 10

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 11
<211> LENGTH: 108
<212> TYPE: PRT
<213> ORGANISM: human

<400> SEQUENCE: 11

Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
                20                  25                  30

Leu Phe Pro Gly Pro Ser Lys Pro Phe Trp Val Leu Val Val Val Gly
            35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser
            100                 105

<210> SEQ ID NO 12
<211> LENGTH: 163
<212> TYPE: PRT
<213> ORGANISM: human

<400> SEQUENCE: 12

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
    115                 120                 125

Gly Glu Arg Arg Arg Gly Lys Gly His Asp Gly Leu Tyr Gln Gly Leu
130                 135                 140

Ser Thr Ala Thr Lys Asp Thr Tyr Asp Ala Leu His Met Gln Ala Leu
145                 150                 155                 160

Pro Pro Arg

<210> SEQ ID NO 13
<211> LENGTH: 492
<212> TYPE: DNA
<213> ORGANISM: human

<400> SEQUENCE: 13
atgaagtgga aggcgctttt caccgcggcc atcctgcagg cacagttgcc gattacagag    60
gcacagagct ttggcctgct ggatcccaaa ctctgctacc tgctggatgg aatcctcttc   120
atctatggtg tcattctcac tgccttgttc ctgagagtga agttcagcag gagcgcagac   180 gccccgcgt accagcaggg ccagaaccag ctctataacg agctcaatct aggacgaaga   240
gaggagtacg atgttttgga caagagacgt ggccgggacc ctgagatggg gggaaagccg   300

```
agaaggaaga acctcagga aggcctgtac aatgaactgc agaaagataa gatggcggag    360
gcctacagtg agattgggat gaaaggcgag cgccggaggg gcaagggggca cgatggcctt   420 taccagggtc tcagtacagc caccaaggac acctacgacg cccttcacat gcaggccctg    480 cccctcgct aa                                                          492
```

```
<210> SEQ ID NO 14
<211> LENGTH: 112
<212> TYPE: PRT
<213> ORGANISM: human

<400> SEQUENCE: 14
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 15
<211> LENGTH: 768
<212> TYPE: DNA
<213> ORGANISM: human

<400> SEQUENCE: 15
atgggaaaca gctgttacaa catagtagcc actctgttgc tggtcctcaa ctttgagagg    60
acaagatcat tgcaggatcc ttgtagtaac tgcccagctg gtacattctg tgataataac   120
aggaatcaga tttgcagtcc ctgtcctcca aatagtttct ccagcgcagg tggacaaagg   180
acctgtgaca tatgcaggca gtgtaaaggt gttttcagga ccaggaagga gtgttcctcc   240
accagcaatg cagagtgtga ctgcactcca gggtttcact gcctgggggc aggatgcagc   300
atgtgtgaac aggattgtaa acaaggtcaa gaactgacaa aaaaaggttg taaagactgt   360
tgctttggga catttaacga tcagaaacgt ggcatctgtc gaccctggac aaactgttct   420 ttggatgaa agtctgtgct gtgaatggg acgaaggaga gggacgtggt ctgtggacca    480
tctccagccg acctctctcc gggagcatcc tctgtgaccc cgcctgcccc tgcgagagag    540
ccaggacact ctccgcagat catctccttc tttcttgcgc tgacgtcgac tgcgttgctc    600
ttcctgctgt tcttcctcac gctccgtttc tctgttgtta acggggcag aaagaaactc    660 ctgtatatat tcaaacaacc atttatgaga ccagtacaaa ctactcaaga ggaagatggc    720
tgtagctgcc gatttccaga agaagaagaa ggaggatgtg aactgtga              768
```

```
<210> SEQ ID NO 16
<211> LENGTH: 600
<212> TYPE: DNA
<213> ORGANISM: human

<400> SEQUENCE: 16
```

```
atgaagtcag gcctctggta tttctttctc ttctgcttgc gcattaaagt tttaacagga      60
gaaatcaatg gttctgccaa ttatgagatg tttatatttc acaacggagg tgtacaaatt     120
ttatgcaaat atcctgacat tgtccagcaa tttaaaatgc agttgctgaa aggggggcaa     180
atactctgcg atctcactaa gacaaaagga agtggaaaca cagtgtccat taagagtctg     240
aaattctgcc attctcagtt atccaacaac agtgtctctt ttttctata caacttggac      300 cattctcatg ccaactatta cttctgcaac ctatcaattt ttgatcctcc tccttttaaa     360
gtaactctta caggaggata tttgcatatt tatgaatcac aactttgttg ccagctgaag     420
ttctggttac cataggatg tgcagccttt gttgtagtct gcattttggg atgcatactt      480
atttgttggc ttacaaaaaa gaagtattca tccagtgtgc acgacccctaa cggtgaatac    540 atgttcatga gagcagtgaa cacagccaaa aaatctagac tcacagatgt gaccctataa    600
```

\<210\> SEQ ID NO 17
\<211\> LENGTH: 282
\<212\> TYPE: DNA
\<213\> ORGANISM: human

\<400\> SEQUENCE: 17

```
atgatccatc tgggtcacat cctcttcctg cttttgctcc cagtggctgc agctcagacg      60
accccaggag agagatcatc actccctgcc ttttaccctg gcacttcagg ctcctgttcc     120
ggatgtgggt ccctctctct gccgctcctg caggcctcg tggctgctga tgcggtggca     180
tcgctgctca tcgtggggc ggtgttcctg tgcgcacgcc cacgccgcag ccccgcccaa      240
gaagatggca agtctacat caacatgcca ggcaggggct ga                        282
```

\<210\> SEQ ID NO 18
\<211\> LENGTH: 24
\<212\> TYPE: DNA
\<213\> ORGANISM: artificial
\<220\> FEATURE:
\<223\> OTHER INFORMATION: scFV 4-1BB fusion primer

\<400\> SEQUENCE: 18

```
gcggccgcac catctccagc cgac                                             24
```

\<210\> SEQ ID NO 19
\<211\> LENGTH: 24
\<212\> TYPE: DNA
\<213\> ORGANISM: 4-1BB zeta fusion primer

\<400\> SEQUENCE: 19

```
cttcactctc agttcacatc cttc                                             24
```

\<210\> SEQ ID NO 20
\<211\> LENGTH: 27
\<212\> TYPE: DNA
\<213\> ORGANISM: artificial
\<220\> FEATURE:
\<223\> OTHER INFORMATION: scFv ICOS fusion primer

\<400\> SEQUENCE: 20

```
gcggccgcac tatcaatttt tgatcct                                          27
```

\<210\> SEQ ID NO 21
\<211\> LENGTH: 27
\<212\> TYPE: DNA
\<213\> ORGANISM: artificial
\<220\> FEATURE:

-continued

```
<223> OTHER INFORMATION: ICOS zeta fusion primer

<400> SEQUENCE: 21
cttcactctt agggtcacat ctgtgag                                        27

<210> SEQ ID NO 22
<211> LENGTH: 24
<212> TYPE: DNA
<213> ORGANISM: artificial
<220> FEATURE:
<223> OTHER INFORMATION: scFV DAP-10 fusion primer

<400> SEQUENCE: 22
gcggccgcac agacgacccc agga                                           24

<210> SEQ ID NO 23
<211> LENGTH: 25
<212> TYPE: DNA
<213> ORGANISM: artificial
<220> FEATURE:
<223> OTHER INFORMATION: DAP-10 zeta fusion primer

<400> SEQUENCE: 23
cttcactctg cccctgcctg gcatg                                          25
```

The invention claimed is:

1. A nucleic acid polymer encoding a chimeric T cell receptor, said chimeric T cell receptor comprising
    (a) a zeta chain portion comprising the intracellular domain of human CD3 ζ chain,
    (b) a costimulatory signaling region, and
    (c) a binding element that specifically interacts with a selected target, wherein the costimulatory signaling region comprises the amino acid sequence encoded by SEQ ID NO:6.

2. The nucleic acid polymer of claim 1, wherein the binding element is an antibody.

3. The nucleic acid polymer of claim 2, wherein the antibody is a single chain antibody.

4. The nucleic acid polymer of claim 3, wherein the single chain antibody binds to prostate specific membrane antigen.

5. The nucleic acid polymer of claim 3, wherein the single chain antibody binds to CD19.

6. The nucleic acid polymer of claim 3, wherein the encoded T cell receptor comprises binding element-costimulatory signaling region-zeta chain portion in that order.

7. The nucleic acid polymer of claim 1, wherein the zeta chain portion comprises the sequence obtained by amplification of human zeta chain DNA with the primers of SEQ ID Nos 1 and 2.

8. The nucleic acid polymer of claim 7, wherein the binding element is an antibody.

9. The nucleic acid polymer of claim 8, wherein the antibody is a single chain antibody.

10. The nucleic acid polymer of claim 9, wherein the single chain antibody binds to prostate specific membrane antigen.

11. The nucleic acid polymer of claim 9, wherein the single chain antibody binds to CD19.

12. The nucleic acid polymer of claim 9, wherein the encoded T cell receptor comprises binding element-costimulatory signaling region-zeta chain portion in that order.

13. The nucleic acid polymer of claim 1, wherein the encoded T cell receptor comprises binding element-signaling region-zeta chain portion in that order.

* * * * *

UNITED STATES PATENT AND TRADEMARK OFFICE
CERTIFICATE OF CORRECTION

PATENT NO. : 7,446,190 B2
APPLICATION NO. : 10/448256
DATED : November 4, 2008
INVENTOR(S) : Sadelain et al.

Page 1 of 1

It is certified that error appears in the above-identified patent and that said Letters Patent is hereby corrected as shown below:

In the Specifications:

Column 15, Line(s) 14-19 should read

<210> 4
<211> 26
<212> DNA
<213> human

<400> 4
ggcggccgca attgaagtta tgtatc 26

Column 15, Line(s) 26-36 should read

<210> 6
<211> 321
<212> DNA
<213> human

<400> 6
attgaagtta tgtatcctcc tccttaccta gacaatgaga agagcaatgg aaccattatc 60
catgtgaaag ggaaacacct ttgtccaagt cccctatttc ccggaccttc taagcccttt 120
tgggtgctgg tggtggttgg tggagtcctg gcttgctata gcttgctagt aacagtggcc 180
tttattattt tctgggtgag gagtaagagg agcaggctcc tgcacagtga ctacatgaac 240
atgactcccc gccgccccgg gcccacccgc aagcattacc agccctatgc cccaccacgc 300
gacttcgcag cctatcgctc c321

Signed and Sealed this
Sixteenth Day of July, 2013

Teresa Stanek Rea
*Acting Director of the United States Patent and Trademark Office*